United States Patent
Koide et al.

(10) Patent No.: US 11,179,113 B2
(45) Date of Patent: Nov. 23, 2021

(54) PRESENTATION METHOD, PRESENTATION DEVICE, AND COMPUTER READABLE MEDIUM

(71) Applicant: ARKRAY, Inc., Kyoto (JP)

(72) Inventors: Keiko Koide, Tokyo (JP); Atsushi Wada, Kyoto (JP); Hideaki Takeda, Kyoto (JP)

(73) Assignee: ARKRAY, Inc., Kyoto (JP)

(*) Notice: Subject to any disclaimer, the term of this patent is extended or adjusted under 35 U.S.C. 154(b) by 760 days.

(21) Appl. No.: 16/035,057

(22) Filed: Jul. 13, 2018

(65) Prior Publication Data

US 2019/0015054 A1    Jan. 17, 2019

(30) Foreign Application Priority Data

Jul. 14, 2017  (JP) ............... JP2017-138391
Jul. 12, 2018  (JP) ............... JP2018-132125

(51) Int. Cl.
*A61B 5/00* (2006.01)
*A61B 5/145* (2006.01)
(Continued)

(52) U.S. Cl.
CPC ........... *A61B 5/74* (2013.01); *A61B 5/14503* (2013.01); *A61B 5/14532* (2013.01);
(Continued)

(58) Field of Classification Search
CPC ... A61B 5/74; A61B 5/14503; A61B 5/14532; A61B 5/6826; G16H 50/20; G16H 40/60
(Continued)

(56) References Cited

U.S. PATENT DOCUMENTS

2009/0054753 A1   2/2009  Robinson et al.
2010/0069730 A1*  3/2010  Bergstrom ............ G16H 40/67
                                                                 600/365
(Continued)

FOREIGN PATENT DOCUMENTS

JP   2016-133890 A   7/2016
JP   2017-515520 A   6/2017
WO   2014/106263 A2  7/2014

OTHER PUBLICATIONS

Communication pursuant to Article 94(3) EPC issued by the European Patent Office dated Oct. 12, 2020, which corresponds to European Patent Application No. 18 183 371.6-1126 and is related to U.S. Appl. No. 16/035,057.

(Continued)

*Primary Examiner* — Kerri L McNally
(74) *Attorney, Agent, or Firm* — Studebaker & Brackett PC

(57) ABSTRACT

A presentation method for presenting a time period to measure a blood glucose level, the presentation method includes: acquiring first information, the first information including a measurement result in which a glucose level of a user is measured with a time interval using a first measurement device and a measurement time at which the measurement result was acquired; determining, based on a comparison result obtained by comparing the first information with a predetermined threshold of the glucose level and a preset period, the time period for the user to measure the blood glucose level by using a second measurement device; and presenting the time period at a display.

8 Claims, 13 Drawing Sheets

(51) Int. Cl.
   *G16H 40/60* (2018.01)
   *G16H 50/20* (2018.01)
   *G16H 20/17* (2018.01)

(52) U.S. Cl.
   CPC ........... *A61B 5/6826* (2013.01); *G16H 40/60* (2018.01); *G16H 50/20* (2018.01); *G16H 20/17* (2018.01)

(58) Field of Classification Search
   USPC .......................................................... 702/19
   See application file for complete search history.

(56) References Cited

U.S. PATENT DOCUMENTS

| | | | | |
|---|---|---|---|---|
| 2011/0053121 | A1* | 3/2011 | Heaton | A61B 5/14532 |
| | | | | 434/127 |
| 2015/0018633 | A1* | 1/2015 | Kovachev | A61B 5/0022 |
| | | | | 600/301 |
| 2015/0289823 | A1* | 10/2015 | Rack-Gomer | A61B 5/165 |
| | | | | 600/365 |
| 2016/0331285 | A1 | 11/2016 | Choi et al. | |

OTHER PUBLICATIONS

Extended European Search Report issued by the European Patent Office dated Dec. 10, 2018, which corresponds to European Patent Application No. 18 18 3371.

\* cited by examiner

FIG.3

| BLOOD SUGAR LEVEL (mg/dL) | MEASUREMENT TIME |
|---|---|
| 100 | 2017/04/07 18:00:00 |
| 110 | 2017/04/07 19:55:30 |
| 90 | 2017/04/08 06:15:17 |
| ⋮ | ⋮ |

| BLOOD SUGAR LEVEL (mg/dL) | MEASUREMENT TIME |
|---|---|
| 100 | 2017/04/07 15:00:00 |
| 101 | 2017/04/07 15:05:00 |
| 101 | 2017/04/07 15:10:00 |
| ⋮ | ⋮ |

※ LOW BLOOD SUGAR/HIGH BLOOD SUGAR REGION TIME BANDS DISPLAYED AS TIME BANDS REQUIRING MEASUREMENTS

PLEASE TAKE MEASUREMENTS FOR TIME BAND STARTING AT 12:40 (0 OCCURRENCES OF LOW BLOOD SUGAR, 12 OCCURRENCES OF HIGH BLOOD SUGAR)

PLEASE TAKE MEASUREMENTS FOR TIME BAND STARTING AT 21:15 (2 OCCURRENCES OF LOW BLOOD SUGAR, 3 OCCURRENCES OF HIGH BLOOD SUGAR)

PLEASE TAKE MEASUREMENTS FOR TIME BAND STARTING AT 23:00 (2 OCCURRENCES OF LOW BLOOD SUGAR, 4 OCCURRENCES OF HIGH BLOOD SUGAR)

THRESHOLD FOR LOW BLOOD SUGAR STATE: [30] MINUTES OR LONGER BELOW [70] mg/dL

THRESHOLD FOR HIGH BLOOD SUGAR STATE: [30] MINUTES OR LONGER AT [150] mg/dL OR HIGHER

[RECALCULATE SMBG MEASUREMENT POINTS]

FIG.10

※ LOW BLOOD SUGAR/HIGH BLOOD SUGAR REGION TIME BANDS DISPLAYED AS TIME BANDS REQUIRING MEASUREMENTS

PLEASE TAKE MEASUREMENTS FOR TIME BAND STARTING AT 12:40 (0 OCCURRENCES OF LOW BLOOD SUGAR, 12 OCCURRENCES OF HIGH BLOOD SUGAR)

PLEASE TAKE MEASUREMENTS FOR TIME BAND STARTING AT 21:15 (2 OCCURRENCES OF LOW BLOOD SUGAR, 3 OCCURRENCES OF HIGH BLOOD SUGAR)

PLEASE TAKE MEASUREMENTS FOR TIME BAND STARTING AT 23:00 (2 OCCURRENCES OF LOW BLOOD SUGAR, 4 OCCURRENCES OF HIGH BLOOD SUGAR)

LOW BLOOD SUGAR FOR 75 MINUTES FROM 21:38:00 ON 04/18/2017 TO 22:53:00 ON 04/18/2017
LOW BLOOD SUGAR FOR 60 MINUTES FROM 21:36:00 ON 04/20/2017 TO 22:36:00 ON 04/20/2017
HIGH BLOOD SUGAR FOR 75 MINUTES FROM 21:39:00 ON 04/08/2017 TO 22:54:00 ON 04/08/2017
HIGH BLOOD SUGAR FOR 30 MINUTES FROM 22:21:00 ON 04/10/2017 TO 22:51:00 ON 04/10/2017
HIGH BLOOD SUGAR FOR 75 MINUTES FROM 21:31:00 ON 04/13/2017 TO 22:46:00 ON 04/13/2017

THRESHOLD FOR LOW BLOOD SUGAR STATE: [30] MINUTES OR LONGER BELOW [70] mg/dL

THRESHOLD FOR HIGH BLOOD SUGAR STATE: [30] MINUTES OR LONGER AT [150] mg/dL OR HIGHER

[RECALCULATE SMBG MEASUREMENT POINTS]

FIG.12

※ FOR MEASUREMENT TIME BANDS IN WHICH NUMBER OF SMBG MEASUREMENTS IS LESS THAN SPECIFIED NUMBER OF MEASUREMENTS, LOW BLOOD SUGAR/HIGH BLOOD SUGAR REGION TIME BANDS ARE DISPLAYED AS TIME BANDS REQUIRING MEASUREMENTS

PLEASE TAKE MEASUREMENTS FOR TIME BAND STARTING AT 12:40 (1 SMBG MEASUREMENT, 0 OCCURRENCES OF LOW BLOOD SUGAR, 12 OCCURRENCES OF HIGH BLOOD SUGAR)

PLEASE TAKE MEASUREMENTS FOR TIME BAND STARTING AT 21:15 (0 SMBG MEASUREMENTS, 2 OCCURRENCES OF LOW BLOOD SUGAR, 3 OCCURRENCES OF HIGH BLOOD SUGAR)

PLEASE TAKE MEASUREMENTS FOR TIME BAND STARTING AT 23:00 (0 SMBG MEASUREMENTS, 2 OCCURRENCES OF LOW BLOOD SUGAR, 4 OCCURRENCES OF HIGH BLOOD SUGAR)

→ NUMBER OF SMBG MEASUREMENTS: [1] OR FEWER PER TIME BAND

→ THRESHOLD FOR LOW BLOOD SUGAR STATE: [30] MINUTES OR LONGER BELOW [70] mg/dL

→ THRESHOLD FOR HIGH BLOOD SUGAR STATE: [30] MINUTES OR LONGER AT [150] mg/dL OR HIGHER

[RECALCULATE SMBG MEASUREMENT POINTS]

PRESENTATION METHOD, PRESENTATION DEVICE, AND COMPUTER READABLE MEDIUM

CROSS-REFERENCE TO RELATED APPLICATION

This application claims priority under 35 USC 119 from Japanese Patent Application No. 2017-138391, filed on Jul. 14, 2017, and Japanese Patent Application No. 2018-132125, filed on Jul. 12, 2018, the disclosures of which are incorporated by reference herein.

BACKGROUND

Technical Field

The present disclosure relates to a presentation method, a presentation device, and a non-transitory computer readable medium storing a presentation program that present a blood glucose level measurement time period.

Related Art

Various measurement devices are known for measuring the blood glucose level of a user who is, for example, a diabetes sufferer. For example, known blood glucose level measurement devices include measurement devices in which blood obtained by pricking one's own fingertip is applied to a sensor in order to measure blood glucose level (see, for example, Japanese Patent Application Laid-Open (JP-A) No. 2016-133890). As an example of such measurement devices, measurement devices employed for what is referred to as Self Monitoring of Blood Glucose (SMBG) are known. This type of measurement device is referred to hereafter as a "blood glucose self-measurement device".

Moreover, for example, known measurement devices for measuring blood glucose level including glucose level include measurement devices that use a sensor or the like attached to the skin of the user to automatically measure the glucose level of the user at predetermined time intervals on a continuing basis (see, for example, Japanese National-Phase Publication No. 2017-515520). Measurement devices employed in what are referred to as Continuous Glucose Monitoring (CGM) and Flash Glucose Monitoring (FGM) are examples of such measurement devices. This type of measurement device is referred to hereafter as a "continuous blood glucose measurement device".

In order to identify fluctuations in the blood glucose level of a user, blood glucose level needs to be continuously measured. Continuous blood glucose measurement devices are therefore preferable. However, as described above, when using a continuous blood glucose measurement device, the sensor has to be attached to the skin at all times for as long as measurements are being taken. The user may find the sensor annoying, and it may be difficult to keep the sensor attached. Moreover, the costs associated with measuring using a continuous blood glucose measurement device are currently higher than the costs associated with measuring using a blood glucose self-measurement device.

Currently, more people use blood glucose self-measurement devices than continuous blood glucose measurement device to measure their own blood glucose level. However, continuous measurements are difficult to achieve when taking measurements using a blood glucose self-measurement device, and generally users take temporal measurements at arbitrary time periods. Measurements are not necessarily taken at time periods when the user is in a high blood glucose state or a low blood glucose state, and sometimes a user may be unable to take measurements at appropriate time periods.

SUMMARY

The present disclosure provides a presentation method, presentation device, and a non-transitory computer readable medium storing a presentation program that may present to a user with an appropriate time period at which to measure their blood glucose level.

A first aspect of the present disclosure is a presentation method for presenting a time period to measure a blood glucose level, the presentation method including: acquiring first information, the first information including a measurement result in which a glucose level of a user is measured with a time interval using a first measurement device and a measurement time at which the measurement result was acquired; determining, based on a comparison result obtained by comparing the first information with a predetermined threshold of the glucose level and a preset period, the time period for the user to measure the blood glucose level by using a second measurement device; and presenting the time period at a display.

In a second aspect of the present disclosure, in the above-described first aspect, determining the time period may include: comparing the first information with a first threshold value which is the predetermined threshold of the glucose level and a first set period which is the preset period; and determining a first period as the time period in a case in which the first period is equal to or longer than the first set period, the first period being a period in which the glucose level included in the first information is continuously equal to or lower than the first threshold value.

In a third aspect of the present disclosure, in the above-described first aspect, determining the time period may include: comparing the first information with a second threshold value which is the predetermined threshold of the glucose level and a second set period which is the preset period; and determining a second period as the time period in a case in which the second period is equal to or longer than the second set period, the second period being a period in which the glucose level included in the first information is continuously equal to or greater than the second threshold value.

In a fourth aspect of the present disclosure, in any one of the above-described aspects, the time period may be determined for each of plural time bands obtained by dividing one day into the plural time bands.

A fifth aspect of the present disclosure, in the above-described fourth aspect, may further include: acquiring second information, the second information including a measurement result for a blood glucose level of the user by the second measurement device and a measurement time at which the measurement result was acquired; determining, based on the second information, a number of measurements measured by the second measurement device for each of the plural time bands; and in a case in which there is a time band that has a number of measurements that is equal to or fewer than a predetermined number of measurements, determining the time period for each time band that has a number of measurements that is equal to or fewer than the predetermined number of measurements.

In a sixth aspect of the present disclosure, in any one of the above-described aspects, the first measurement device may be a device that employs a sensor attached to skin of the user to measure glucose levels.

In a seventh aspect of the present disclosure, in any one of the first to fifth aspects, the first measurement device may be a device that employs a sensor to measure glucose levels in an interstitial fluid of the user, and that may be used for Continuous Glucose Monitoring (CGM) or Flash Glucose Monitoring (FGM).

In an eighth aspect of the present disclosure, in any one of the above-described aspects, the second measurement device may be a device used for Self Monitoring of Blood Glucose (SMBG) used by the user.

A ninth aspect of the present disclosure is a presentation device including: an acquisition section acquiring first information, the first information including a measurement result in which a glucose level of a user is measured with a time interval using a first measurement device and a measurement time at which the measurement result was acquired; a determination section determining, based on a comparison result obtained by comparing the first information with a predetermined threshold of the glucose level and a preset period, a time period for the user to measure a blood glucose level by using a second measurement device; and a presentation section presenting the time period at a display.

A tenth aspect of the present disclosure is a non-transitory computer readable medium storing a program that is executable by a computer to perform a process for presenting a time period to measure a blood glucose level, the process including: acquiring first information, the first information including a measurement result in which a glucose level of a user is measured with a time interval using a first measurement device and a measurement time at which the measurement result was acquired; determining, based on a comparison result obtained by comparing the first information with a predetermined threshold of the glucose level and a preset period, the time period for the user to measure the blood glucose level by using a second measurement device; and presenting the time period at a display.

According to the above aspects, the presentation method, the presentation device, and the non-transitory computer readable medium storing the presentation program of the present disclosure may present to a user with an appropriate time period at which to measure their blood glucose level.

BRIEF DESCRIPTION OF THE DRAWINGS

Exemplary embodiments will be described in detail based on the following figures, wherein:

FIG. 3 is a diagram to explain information stored in a storage section of a blood glucose self-measurement device of an exemplary embodiment;

FIG. 5 is a diagram to explain information stored in a storage section of a continuous blood glucose measurement device of an exemplary embodiment;

FIG. 9 is a diagram illustrating an advice screen displayed on a display of a display device of the first exemplary embodiment;

FIG. 10 is a diagram illustrating a display of advice details on an advice screen displayed on a display of a display device of the first exemplary embodiment;

FIG. 12 is a diagram illustrating an advice screen displayed on a display of a display device of the second exemplary embodiment.

DETAILED DESCRIPTION

First Exemplary Embodiment

Detailed explanation follows regarding a first exemplary embodiment of the present disclosure.

Figure 1:
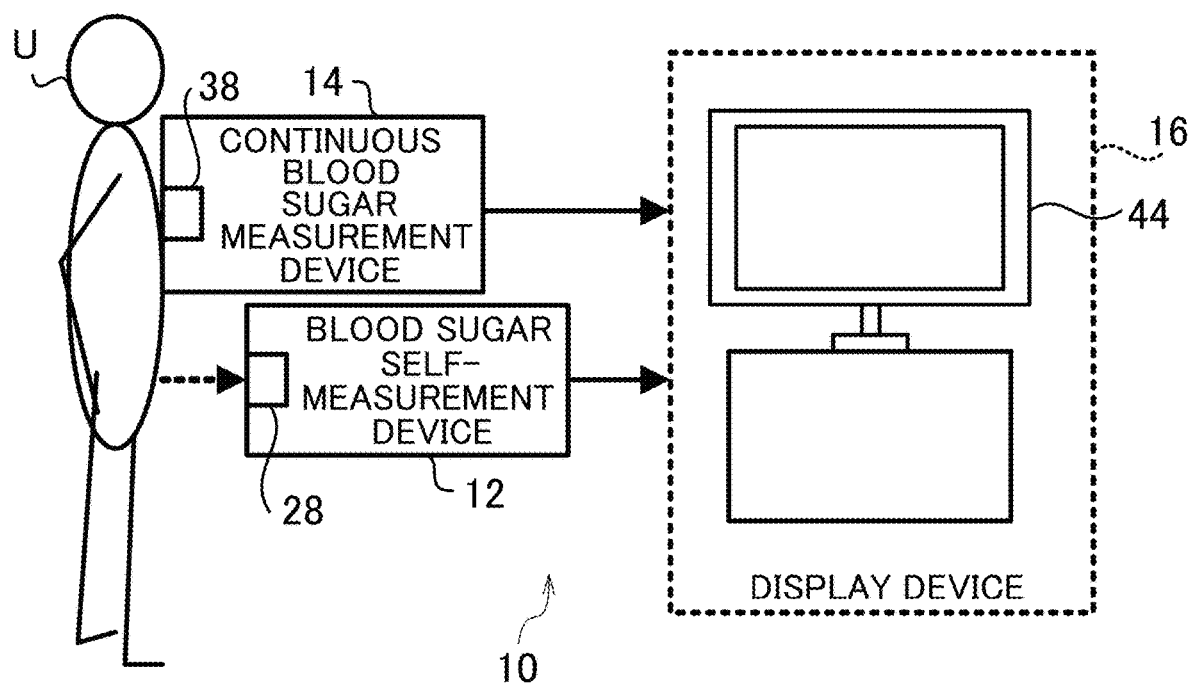
FIG. 1 is a schematic configuration diagram illustrating a configuration of a blood glucose measurement system of an exemplary embodiment.

FIG. 1 is a schematic configuration diagram illustrating a configuration of a blood glucose measurement system 10 of the present exemplary embodiment. As illustrated in FIG. 1, the blood glucose measurement system 10 of the present exemplary embodiment includes a blood glucose self-measurement device 12 to measure a blood glucose level of a user U, a continuous blood glucose measurement device 14 to measure a glucose level of the user U, and a display device 16 that displays the glucose level measurements and the blood glucose level measurements. Note that, as the continuous blood glucose measurement device 14, devices that measures the glucose level (the blood glucose level) within the blood, and devices that measures the glucose level included in interstitial fluid or the like, are known. Generally, a glucose level included in interstitial fluid measured by a continuous blood glucose measurement device is called "the blood glucose level". However, in the present disclosure, the result of the measurement by the continuous blood glucose measurement device 14 is called "the glucose level", and the result of the measurement by the blood glucose self-measurement device 12 is called "the blood glucose level". Further, when representing both the results of the measurement by the continuous blood glucose measurement device 14 and the blood glucose self-measurement device 12, the results will be called "the blood glucose level".

The blood glucose self-measurement device 12 of the present exemplary embodiment is a measurement device in which the user U uses as the SMBG When the user U takes a measurement using the blood glucose self-measurement device 12, blood obtained by the user U by pricking a fingertip is applied to a sensor 28. The blood glucose self-measurement device 12 measures the blood glucose level of the blood applied to the sensor 28, and stores several days' worth of measurement results (for example two weeks' worth in the present exemplary embodiment). The blood glucose level measurements taken by the blood glucose self-measurement device 12 are taken by the user U at given time periods. Examples of the measurement time periods include given time periods such as before meals, after meals, before and after exercise, and before and after going to bed, or any other time period at which the user feels like they would like to know their own blood glucose level.

The blood glucose self-measurement device 12 of the present exemplary embodiment is an example of a second device of the present disclosure.

Figure 2:
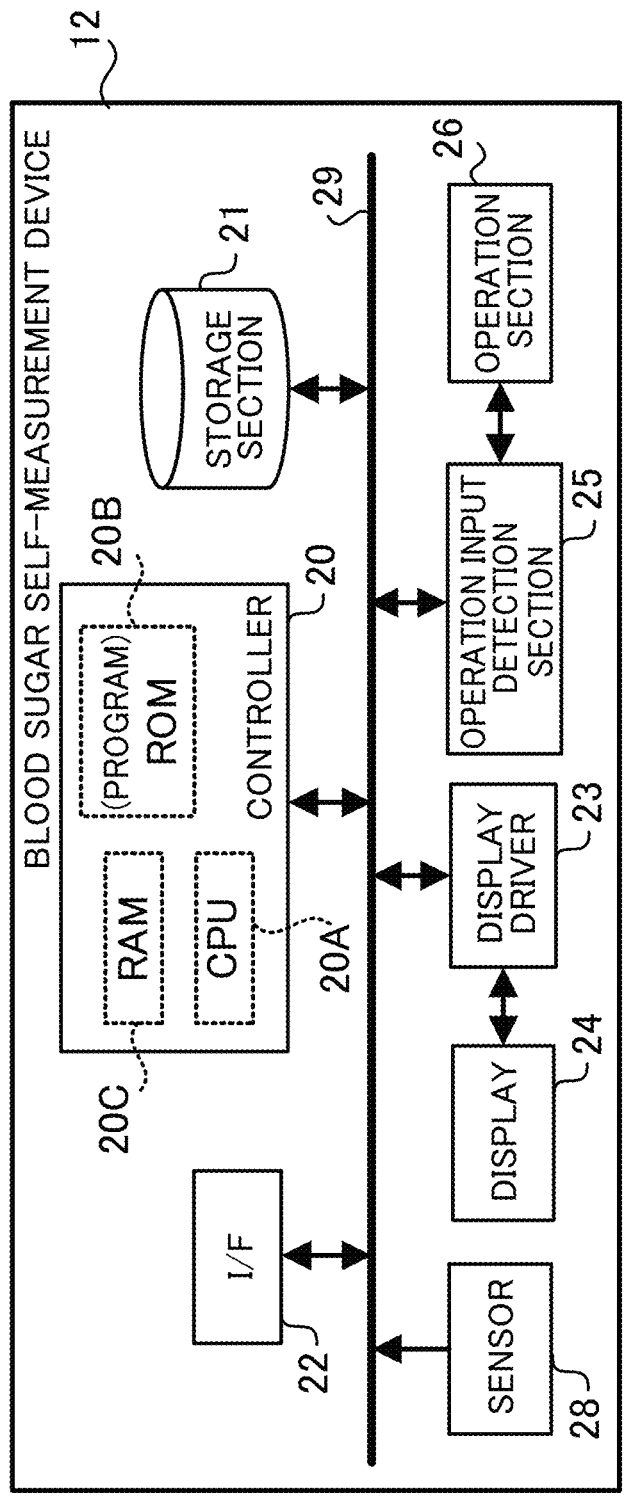
FIG. 2 is a block diagram illustrating a configuration of a blood glucose self-measurement device of an exemplary embodiment.

FIG. 2 is a block diagram illustrating a configuration of the blood glucose self-measurement device 12 of the present exemplary embodiment. As illustrated in FIG. 2, the blood glucose self-measurement device 12 of the present exemplary embodiment includes a controller 20, a storage section 21, an interface (I/F) 22, a display driver 23, a display 24, an operation input detection section 25, an operation section 26, and the sensor 28. The controller 20, the storage section 21, the I/F 22, the display driver 23, the operation input detection section 25, and the sensor 28 are connected to one another through a bus 29.

The controller 20 is what is referred to as a microprocessor, and includes a Central Processing Unit (CPU) 20A, Read Only Memory (ROM) 20B, and Random Access Memory (RAM) 20C. The CPU 20A governs overall operation of the blood glucose self-measurement device 12. The ROM 20B is pre-stored with various programs, various parameters, and the like. The RAM 20C is employed as a work area and the like during execution of the various programs by the CPU 20A.

The storage section 21 is configured by memory such as flash memory, and is stored with blood glucose self-measurement data 21A, including plural pieces of information in which blood glucose levels measured by the user U are associated with measurement times, as illustrated in the example of FIG. 3. As illustrated in FIG. 3, in the present exemplary embodiment, the measurement times stored in the blood glucose self-measurement data 21A include the date and time of the blood glucose level measurement. The blood glucose self-measurement data 21A of the present exemplary embodiment is an example of second information of the present disclosure.

The I/F 22 uses wireless communication or the like to exchange various information with the continuous blood glucose measurement device 14 and the display device 16.

The display 24 displays various information such as blood glucose levels, these being measurement results. The display driver 23 controls the display of this various information on the display 24. The operation section 26 is employed by the user U to give instructions relating to blood glucose level measurements and the display of measured blood glucose levels. The operation input detection section 25 detects an operation state of the operation section 26 by the user U, for example. In the present exemplary embodiment, the display 24 is, for example, a liquid crystal monitor, and the operation section 26 is configured by various buttons or the like. However, the configurations of the display 24 and the operation section 26 are not particularly limited, and, for example, the display 24 and the operation section 26 may be configured by an integrated touch panel display.

The sensor 28 has functionality to detect the concentration of glucose, namely the blood glucose level, of the blood applied by the user U. Note that in the present disclosure, the term "blood glucose level" corresponds to the concentration of glucose in the blood. Moreover, in the present disclosure, the term "glucose level" corresponds to the concentration of glucose in a body fluid (including, for example, interstitial fluid), and is not limited to blood.

The continuous blood glucose measurement device 14 of the present exemplary embodiment is a measurement device in which the user U uses as the CGM. When taking measurements using the continuous blood glucose measurement device 14, a sensor unit 38 applied to the skin of the user U automatically measures the glucose level in interstitial fluid with predetermined time intervals on a continuing basis, and several days' worth of measurement results (for example two weeks' worth in the present exemplary embodiment) are stored in the continuous blood glucose measurement device 14. The continuous blood glucose measurement device 14 of the present exemplary embodiment is an example of a first device of the present disclosure.

Figure 4:
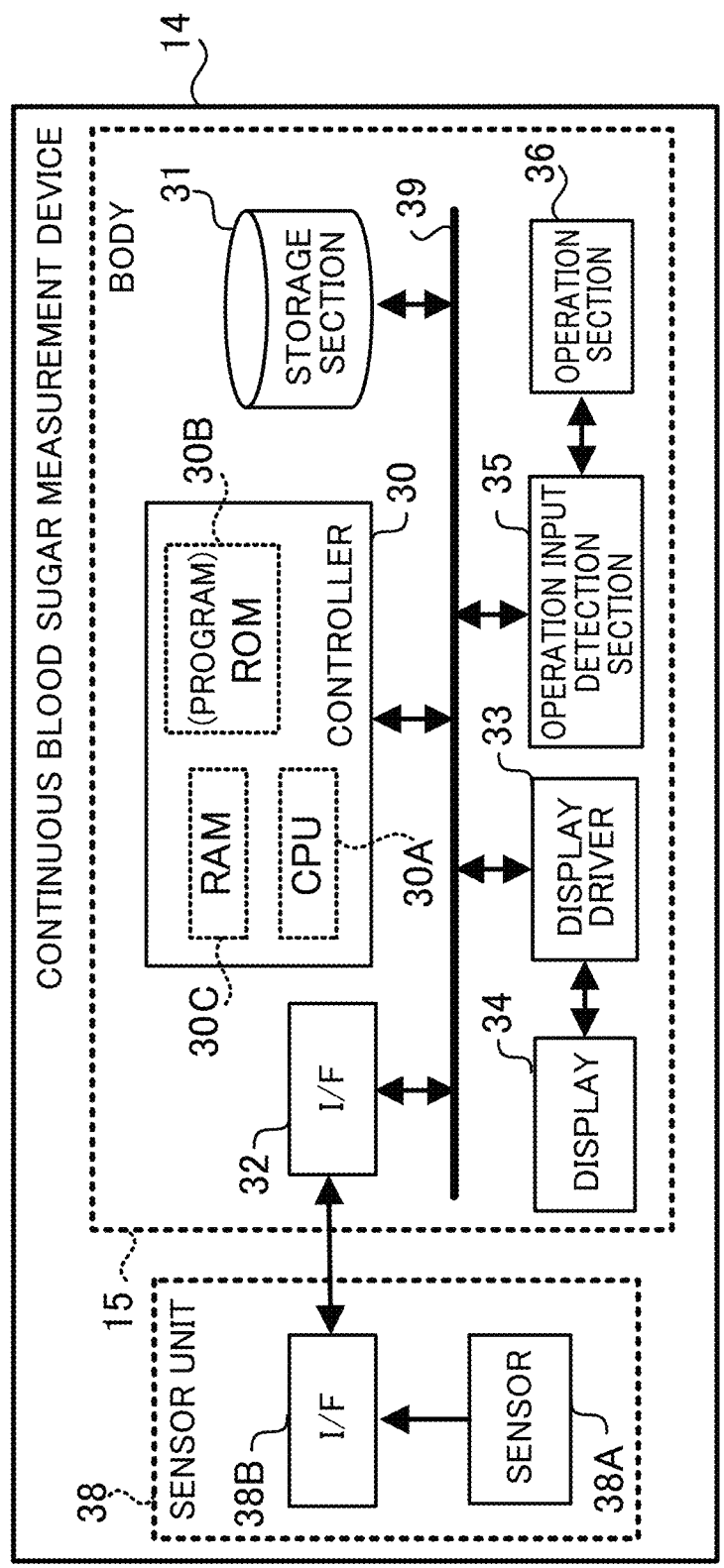
FIG. 4 is a block diagram illustrating a configuration of a continuous blood glucose measurement device of an exemplary embodiment.

FIG. 4 is a block diagram illustrating an example of configuration of the continuous blood glucose measurement device 14 of the present exemplary embodiment. As illustrated in FIG. 4, the continuous blood glucose measurement device 14 of the present exemplary embodiment includes a body 15 and a sensor unit 38. The body 15 includes a controller 30, a storage section 31, an I/F 32, a display driver 33, a display 34, an operation input detection section 35, and an operation section 36. The controller 30, the storage section 31, the I/F 32, the display driver 33, and the operation input detection section 35 are connected to one another through a bus 39.

The controller 30 is what is referred to as a microprocessor, and includes a CPU 30A, ROM 30B, and RAM 30C. The CPU 30A governs overall operation of the continuous blood glucose measurement device 14. The ROM 30B is pre-stored with various programs, various parameters, and the like. The RAM 30C is employed as a work area and the like during execution of the various programs by the CPU 30A.

The storage section 31 is configured by memory such as flash memory, and is stored with continuous blood glucose measurement data 31A, in which glucose levels measured by the sensor unit 38 are associated with measurement times, as illustrated in the example of FIG. 5. As illustrated in FIG. 5, in the present exemplary embodiment, the measurement times stored in the continuous blood glucose measurement data 31A include the date and time of the glucose level measurement. The continuous blood glucose measurement data 31A of the present exemplary embodiment is an example of first information of the present disclosure.

The I/F 32 uses wireless communication or the like to exchange various information with the blood glucose self-measurement device 12 and the display device 16. Moreover, information corresponding to glucose levels detected by a sensor 38A (referred to hereafter simply as "glucose levels") is input to the I/F 32 from an I/F 38B of the sensor unit 38 by wireless communication.

The display 34 displays various information such as blood glucose levels, these being measurement results. The display driver 33 controls the display of this various information on the display 34. The operation section 36 is used by the user U to give instructions relating to the display of measured blood glucose levels. The operation input detection section 35 detects an operation state of the operation section 36 by the user U, for example. In the present exemplary embodiment, the display 34 is, for example, a liquid crystal monitor, and the operation section 36 is configured by various buttons or the like. However, the display 34 and the operation section 36 are not particularly limited, and, for example, the display 34 and the operation section 36 may be configured by an integrated touch panel.

The sensor unit 38 includes the sensor 38A and the I/F 38B. The sensor 38A is attached to the skin of the user U as described above, and detects the glucose level of interstitial fluid in subcutaneous tissue at predetermined time intervals (as an example, at 10 second intervals in the present exemplary embodiment). The glucose levels detected by the sensor 38A are input to the body 15 via the I/F 38B and the I/F 32.

The controller 30 of the body 15 averages the input glucose levels over predetermined time intervals (as an example, over 5 minute intervals in the present exemplary embodiment), and stores information in which the averaged glucose levels are associated with measurement times in the storage section 31 as the continuous blood glucose measurement data 31A.

Note that the continuous blood glucose measurement device 14 of the present exemplary embodiment is routinely input with the blood glucose levels measured by the blood glucose self-measurement device 12 by operation of the operation section 36 by the user U, for example at a frequency of several times per day. Correction (calibration) is performed based on the input blood glucose levels.

The display device 16 is a device to display the blood glucose levels measured by the blood glucose self-measurement device 12 and the glucose levels measured by the continuous blood glucose measurement device 14. The display device 16 is also a device to present the user U with advice relating to appropriate time periods at which to measure their own blood glucose using the blood glucose self-measurement device 12, based on the glucose levels measured by the continuous blood glucose measurement device 14. In the present exemplary embodiment, the display device 16 is operated by a doctor or the like (referred to hereafter simply as "doctor"). Note that the display device 16 of the present exemplary embodiment is an example of a presentation device of the present disclosure.

Figure 6:
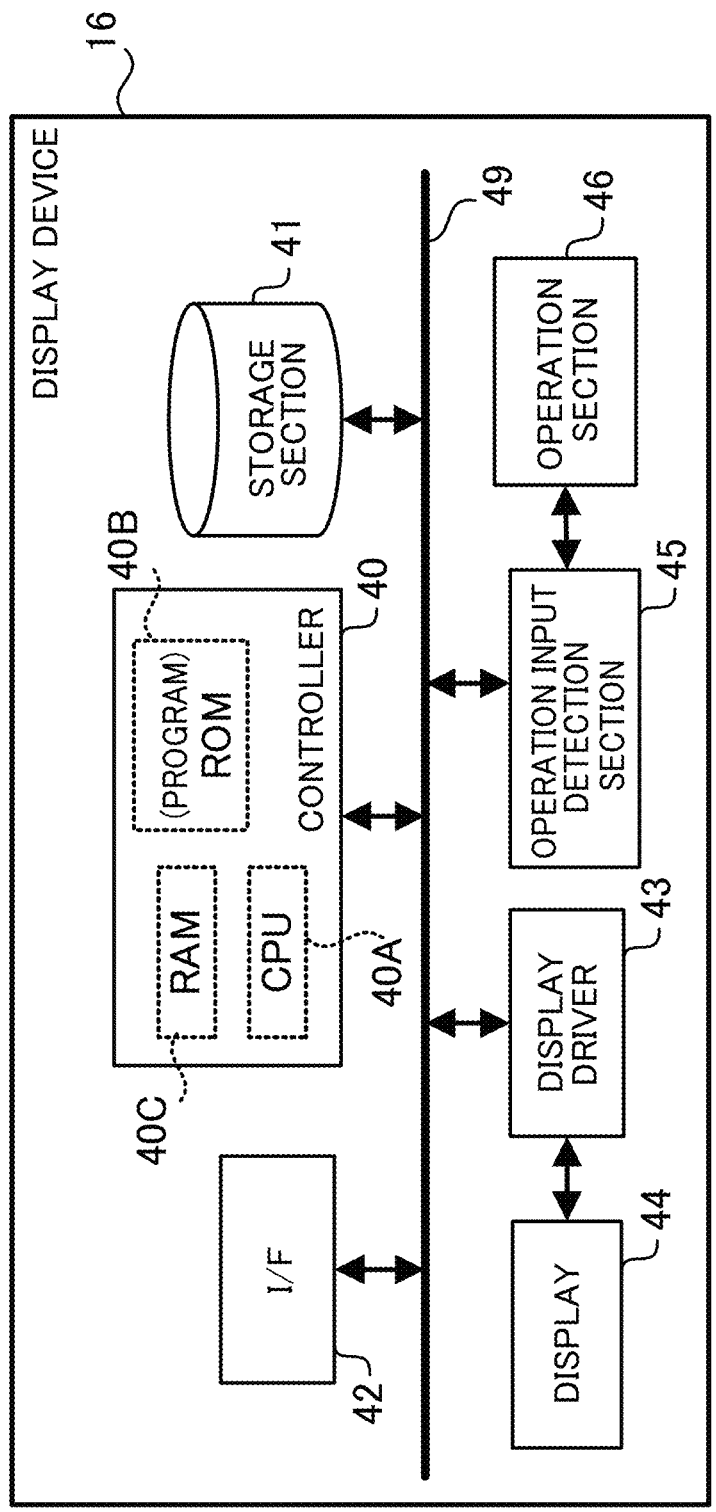
FIG. 6 is a block diagram illustrating a configuration of a display device of an exemplary embodiment.

FIG. 6 is a block diagram illustrating an example of configuration of the display device 16 of the present exemplary embodiment. As illustrated in FIG. 6, the display device 16 includes a controller 40, a storage section 41, an I/F 42, a display driver 43, a display 44, an operation input detection section 45, and an operation section 46.

The controller 40 includes a CPU 40A, ROM 40B, and RAM 40C. The CPU 40A governs overall operation of the display device 16. The ROM 40B is pre-stored with various programs including a presentation program of the present disclosure, various parameters, and the like. The RAM 40C is employed as a work area and the like during execution of the various programs by the CPU 40A.

The storage section 41 is a non-volatile storage section such as a Hard Disk Drive (HDD). The storage section 41 of the present exemplary embodiment stores the blood glucose self-measurement data 21A input from the blood glucose self-measurement device 12 and continuous blood glucose measurement data 31A input from the continuous blood glucose measurement device 14.

The I/F 42 uses wireless communication or the like to exchange various information with the blood glucose self-measurement device 12 and the continuous blood glucose measurement device 14.

The display 44 displays various information such as blood glucose levels, these being measurement results. The display driver 43 controls to display various information on the display 44. The operation section 46 is employed by the doctor to give instructions relating to the display of blood glucose levels. The operation input detection section 45 detects an operation state of the operation section 46 by the doctor. In the present exemplary embodiment, the display 44 is, for example, a liquid crystal monitor, and the operation section 46 is configured by a keyboard, a mouse, various buttons, and the like. However, the configurations of the display 44 and the operation section 46 are not particularly limited, and, for example, the display 44 and the operation section 46 may be configured by an integrated touch panel.

Next, explanation follows regarding operation of the present exemplary embodiment.

As described above, the user U uses the blood glucose self-measurement device 12 to measure the blood glucose level of blood obtained by pricking their own fingertip at given time periods, several times a day. The user U also attaches the sensor unit 38 of the continuous blood glucose measurement device 14 to their skin, and the glucose level is measured automatically by the continuous blood glucose measurement device 14 at predetermined time intervals on a continuing basis. The user U visits the doctor, who is in possession of the display device 16, taking with them the blood glucose self-measurement device 12 and the continuous blood glucose measurement device 14 stored with several days' worth of measurement results (around two weeks' worth as an example in the present exemplary embodiment).

When the doctor connects the blood glucose self-measurement device 12 and the display device 16 together through a wireless or wired connection, the blood glucose self-measurement data 21A stored in the storage section 21 of the blood glucose self-measurement device 12 is input from the blood glucose self-measurement device 12 to the display device 16, and stored in the storage section 41. Similarly, when the doctor connects the continuous blood glucose measurement device 14 and the display device 16 together through a wireless or wired connection, the continuous blood glucose measurement data 31A stored in the storage section 31 of the continuous blood glucose measurement device 14 is input from the continuous blood glucose measurement device 14 to the display device 16, and stored in the storage section 41.

Based on the blood glucose self-measurement data 21A (second information) stored in the storage section 41, the controller 40 of the display device 16 generates a daily fluctuation graph expressing fluctuations in the blood glucose levels measured by the blood glucose self-measurement device 12 over the course of a day (this is referred to hereafter as the "self-measurement daily fluctuation graph 52"), and displays the self-measurement daily fluctuation graph on the display 44. The methods used to generate and display the self-measurement daily fluctuation graph 52 are not particularly limited, and, for example, the method disclosed in JP-A No. 2016-133890 may be employed.

Based on the continuous blood glucose measurement data 31A (first information) stored in the storage section 41, the controller 40 of the display device 16 also generates a daily fluctuation graph, expressing fluctuations in the glucose levels measured by the continuous blood glucose measurement device 14 over the course of a day (this is referred to hereafter as the "continuous measurement daily fluctuation graph 54"), and displays the continuous measurement daily fluctuation graph on the display 44. The methods used to generate and display the continuous measurement daily fluctuation graph 54 are not particularly limited, and, for example, the method disclosed in JP-A No. 2017-515520 may be employed.

Figure 7:
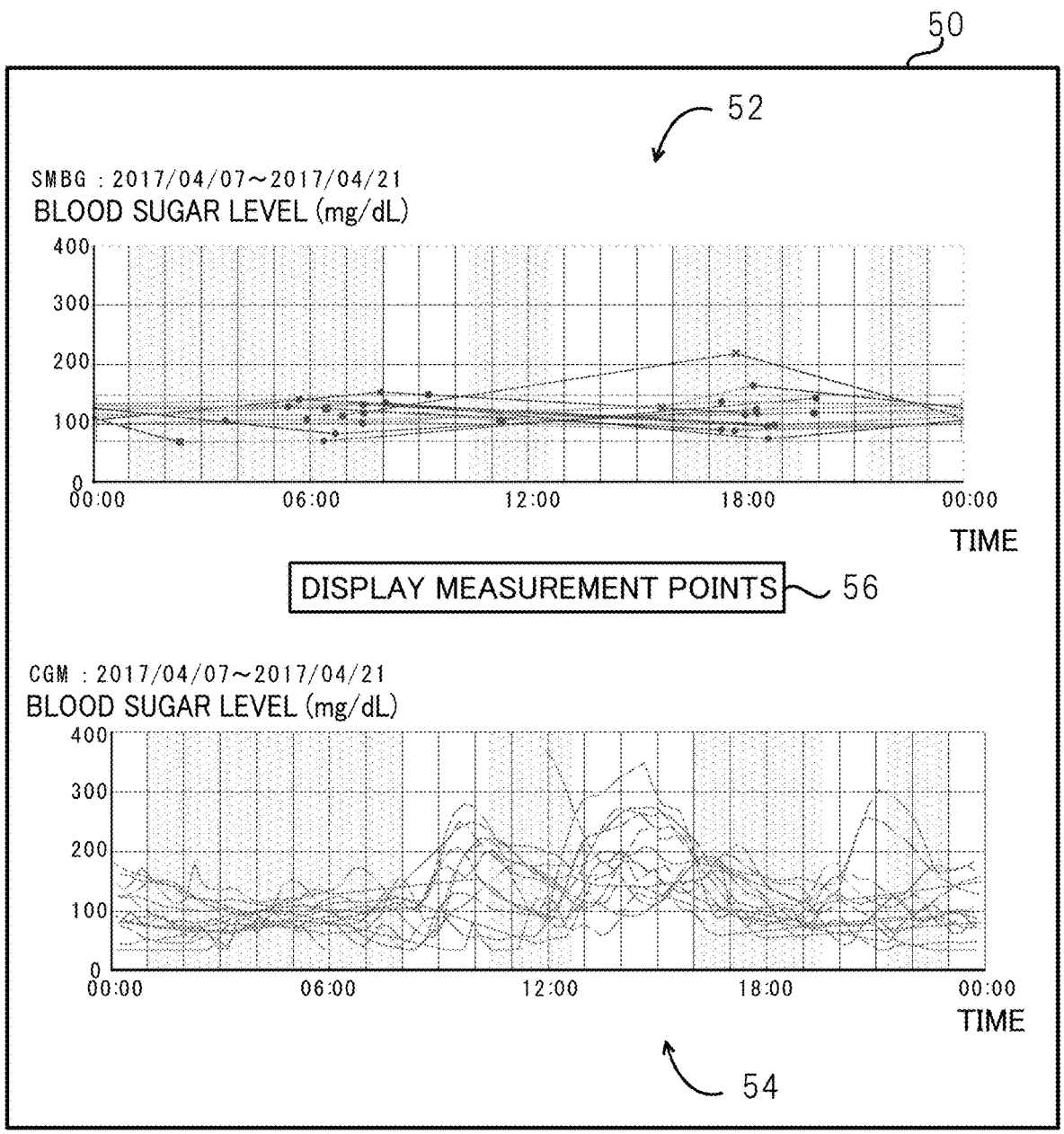
FIG. 7 is a diagram illustrating a daily fluctuation graph display screen of an exemplary embodiment.

The display device 16 of the present exemplary embodiment displays the self-measurement daily fluctuation graph 52 and the continuous measurement daily fluctuation graph 54 side-by-side on the same screen on the display 44. FIG. 7 illustrates an example of a daily fluctuation graph display screen 50 displaying a self-measurement daily fluctuation graph 52 and a continuous measurement daily fluctuation graph 54.

As illustrated in FIG. 7, in the self-measurement daily fluctuation graph 52, blood glucose level fluctuations are represented by a single line for each measurement day. Lines representing the fluctuations for each measurement day are displayed superimposed on one another in a single graph with a common time axis. Similarly, as illustrated in FIG. 7, in the continuous measurement daily fluctuation graph 54, fluctuations of the glucose level are represented by a single line for each measurement day, and lines representing the fluctuations for each measurement day are displayed superimposed on one another in a single graph with a common time axis.

The time, this being the parameter along the horizontal axis, is aligned between the self-measurement daily fluctuation graph 52 and the continuous measurement daily fluctuation graph 54 that are displayed on the daily fluctuation graph display screen 50. This enables the doctor and the user U to easily compare the measurement results from the blood glucose self-measurement device 12 and the measurement results from the continuous blood glucose measurement device 14.

Note that in the blood glucose measurement system 10 of the present exemplary embodiment, the blood glucose levels from the blood glucose self-measurement device 12 are managed in time bands, with a single day being divided into plural time bands. The time bands used to manage the blood glucose levels may be set according to the lifestyle of the user U, for example based on mealtimes, bedtime, getting-up time, exercise times, and, in cases in which the user injects insulin, insulin injection time periods. Note that there is no limitation thereto, and time bands may be set by dividing 24 hours into uniform segments from a specific start time. As an example, in the present exemplary embodiment, explanation is given in which blood glucose levels are managed in eight time bands, split at 08:00, 10:20, 12:40, 16:05, 19:30, 21:15, 23:00, and 01:00.

In the daily fluctuation graph display screen 50 illustrated in FIG. 7, when the blood glucose levels in the self-measurement daily fluctuation graph 52 and the continuous measurement daily fluctuation graph 54 are compared for the time band from 12:40 to 16:05, the blood glucose levels in the self-measurement daily fluctuation graph 52 are lower.

Specifically, in the time band from 12:40 to 16:05, although the continuous measurement daily fluctuation graph 54 indicates that the user U had high blood glucose on most measurement days, the self-measurement daily fluctuation graph 52 does not indicate that the user U had high blood glucose on most measurement days. Such differences between the blood glucose levels (different blood glucose level fluctuations) between the self-measurement daily fluctuation graph 52 and the continuous measurement daily fluctuation graph 54 are caused by taking too few blood glucose level measurements using the blood glucose self-measurement device 12 in that time band.

The display device 16 of the present exemplary embodiment has functionality to present appropriate measurement time periods for the user U to measure their blood glucose level using the blood glucose self-measurement device 12, based on the continuous blood glucose measurement data 31A. In the present exemplary embodiment, as illustrated in FIG. 7, when the doctor uses the operation section 46 to press (click on) a button 56 displayed on the daily fluctuation graph display screen 50, the controller 40 executes presentation processing to present measurement time periods (referred to hereafter as "measurement points") for the blood glucose self-measurement device 12.

Figure 8:
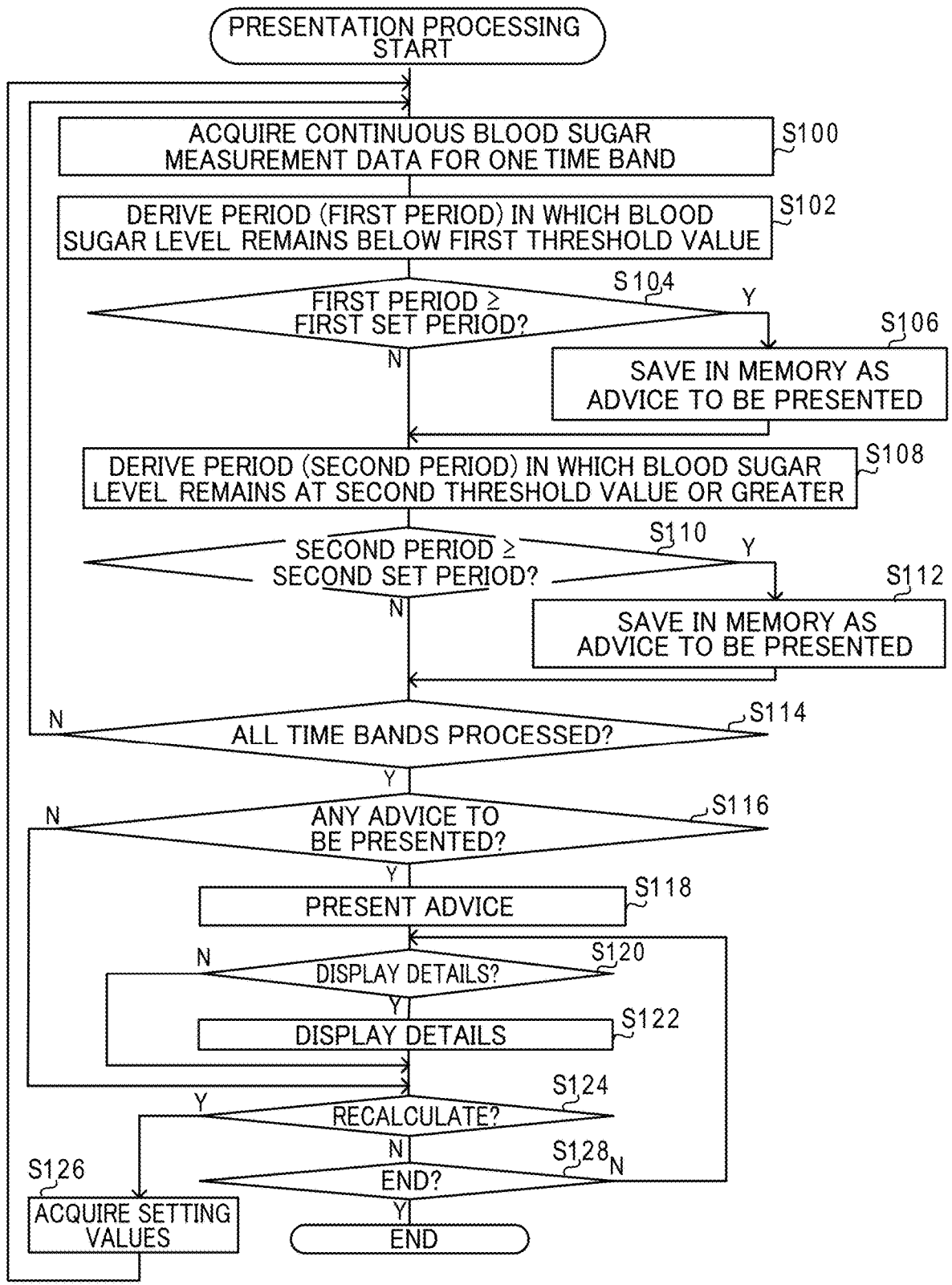
FIG. 8 is a flowchart illustrating a presentation processing executed by a display device of a first exemplary embodiment.

FIG. 8 is a flowchart illustrating a flow of presentation processing executed by the controller 40 of the display device 16 of the present exemplary embodiment. Note that in the present exemplary embodiment, the CPU 40A of the controller 40 executes a presentation program stored in the ROM 40B to execute the presentation processing illustrated in FIG. 8, such that the controller 40 functions as an example of an acquisition section, a determination section and a presentation section of the present disclosure.

In step S100 in FIG. 8, the controller 40 acquires the continuous blood glucose measurement data 31A for one time band from the storage section 41. For example, the controller 40 acquires the continuous blood glucose measurement data 31A for the time band from 08:00 to 10:20 for each measurement day from the storage section 41.

Next, in step S102, for each measurement day, the controller 40 determines a period during which the glucose level remains below a first threshold value (referred to hereafter as the "first period"), based on the acquired continuous blood glucose measurement data 31A. The first threshold value is a threshold value used to determine whether or not the user U is in a low blood glucose state, and is an example of "predetermined threshold of glucose level". In the present exemplary embodiment, as an example, an initial value of the first threshold value is set in advance. At the start of the presentation processing, the initial value is used to determine the first period. Note that, when determining the first period, if glucose levels that may be considered anomalies arising due to noise or the like are included in the continuous blood glucose measurement data 31A, such anomalies may be ignored.

At the next step S104, the controller 40 determines whether or not the determined first period is a first set period or longer. The first set period is a threshold value used to determine whether or not the user U is in a low blood glucose state, and is an example of "preset period". Namely, in the present exemplary embodiment, the user U is considered to be in a low blood glucose state in cases in which their glucose level remains below the first threshold value for the first set period or longer.

In cases in which the first period is the first set period or longer on even one measurement day, affirmative determination is made in step S104, and processing proceeds to step S106. In step S106, the controller 40 saves information representing the first period in the RAM 40C as measurement point advice to be presented, and then processing proceeds to step S108. In the present exemplary embodiment, as an example, the information representing the first period includes the date and time of the start of the first period, and the date and time of the end of the first period.

In cases in which there is no first period of the first set period or longer on any of the measurement days, namely, in cases in which the first period is shorter than the first set period on all measurement days, negative determination is made in step S104, and processing proceeds to step S108.

In step S108, based on the continuous blood glucose measurement data 31A acquired in step S100, the controller 40 determines a period during in which the glucose level remained at a second threshold value or greater (referred to hereafter as the "second period") for each measurement day. The second threshold value is a threshold value used to determine whether or not the user U is in a high blood glucose state, and is an example of "predetermined threshold of glucose level". In the present exemplary embodiment, as an example, an initial value of the second threshold value is set in advance. At the start of the presentation processing, the initial value is used to determine the second period. Note that when determining the second period, similarly to when determining the first period, if glucose levels that may be considered anomalies arising due to noise or the like are included in the continuous blood glucose measurement data 31A, such anomalies may be ignored.

In next step S110, the controller 40 determines whether or not the determined second period is a second set period or longer. The second set period is a threshold value used to determine whether or not the user U is in a high blood glucose state, and is an example of "preset period". Namely, in the present exemplary embodiment, the user U is considered to be in a high blood glucose state in cases in which their glucose level remains at the second threshold value or higher for the second set period or longer.

In cases in which the second period is the second set period or longer on even one measurement day, affirmative determination is made in step S110, and processing proceeds to step S112. In step S112, the controller 40 saves information representing the second period in the RAM 40C as measurement point advice to be presented, and then processing proceeds to step S114. In the present exemplary embodiment, as an example, the information representing the second period includes the date and time of the start of the second period, and the date and time of the end of the second period.

In cases in which there is no second period of the second set period or longer on any of the measurement days, namely, in cases in which the second period is shorter than the second set period on all measurement days, negative determination is made in step S110, and processing proceeds to step S114.

In next step S114, the controller 40 determines whether or not the processing of steps S100 to S112 has been performed for all of the time bands. In cases in which the processing of steps S100 to S112 has not yet been performed for all of the time bands, negative determination is made in step S114, and processing returns to step S100. The controller 40 then acquires the continuous blood glucose measurement data 31A for a time band for which the processing of steps S100 to S112 has not yet been performed, and executes the processing of steps S100 to S112.

In cases in which the processing of steps S100 to S112 has been performed for all of the time bands, affirmative determination is made in step S114, and processing proceeds to step S116.

In step S116, the controller 40 determines whether or not advice to be presented is present. In cases in which information representing advice to be presented has not been saved in the RAM 40C, negative determination is made in step S116, and processing proceeds to step S124. In cases in which information representing advice to be presented has been saved in the RAM 40C, affirmative determination is made in step S116, and processing proceeds to step S118.

In step S118, based on the information representing advice to be presented saved in the RAM 40C, the controller 40 generates a screen presenting advice on measurement points for taking blood glucose level measurements using the blood glucose self-measurement device 12, and displays this screen on the display 44.

FIG. 9 illustrates an example of an advice screen 60 as an example of a screen presenting advice on measurement points for taking blood glucose level measurements using the blood glucose self-measurement device 12. As an example, advice 63 corresponding to the advice to be presented is displayed in an advice presentation region 62 of the advice screen 60 illustrated in FIG. 9. In the present exemplary embodiment, as illustrated in FIG. 9, the advice 63 displayed includes a time band in which blood glucose level should be measured using the blood glucose self-measurement device 12, a number of occurrences of a low blood glucose state (number of occurrences of a first period) in this time band, and a number of occurrences of a high blood glucose state (number of occurrences of a second period) in this time band.

In next step S120, the controller 40 determines whether or not to display more details. In the present exemplary embodiment, the details of first periods and second periods can be displayed for each of the time bands displayed in the advice presentation region 62. In the present exemplary embodiment, as an example, from the advice 63 displayed in the advice presentation region 62, the doctor uses the operation section 46 to specify a time band for which they want to display more details. The details of the first periods and the second periods in the specified time band are accordingly displayed in a detailed display region 64.

In the present exemplary embodiment, in cases in which the doctor does not specify any of the time bands included in the advice 63 displayed in the advice presentation region 62, negative determination is made in step S120, and processing proceeds to step S124. In cases in which the doctor specifies one of the time bands included in the advice 63 displayed in the advice presentation region 62, affirmative determination is made in step S120, and processing proceeds to step S122.

In step S122, the controller 40 references the RAM 40C to generate detailed information 65 representing details of the first periods and the second periods in the specified time band, and displays the detailed information 65 in the detailed display region 64 of the advice screen 60.

The example illustrated in FIG. 10 illustrates a state in which the doctor has specified display of details for the time band starting at 21:15 from out of the advice 63 displayed in the advice presentation region 62. In the example illustrated in FIG. 10, in the time band starting at 21:15, there are two occurrences of low blood glucose, and three occurrences of high blood glucose. Accordingly, in the example illustrated in FIG. 10, detailed information 65 including details of the two occurrences of the first period and details of the three occurrences of the second period is displayed in the detailed display region 64.

In next step S124, the controller 40 determines whether or not to recalculate measurement points. In the present exemplary embodiment, measurement points can be recalculated based on a first threshold value, a first set period, a second threshold value, and a second set period that have been updated by the doctor. Accordingly, in the example illustrated in FIG. 10, update information 66 for updating the first threshold value and the first set period used to determine a low blood glucose state, and update information 68 for updating the second threshold value and the second set period used to determine a high blood glucose state, are displayed on the advice screen 60. The update information 66 includes a box 66A for setting the first threshold value, and a box 66B for setting the first set period. The update information 68 includes a box 68A for setting the second threshold value and a box 68B for setting the second set period. The box 66A, the box 66B, the box 68A, and the box 68B respectively display the values that are currently set.

To update the first threshold value, the doctor inputs the desired first threshold value to the box 66A using the operation section 46. To update the first set period, the doctor inputs the desired first set period to the box 66B using the operation section 46. To update the second threshold value, the doctor inputs the desired second threshold value to the box 68A using the operation section 46. To update the second set period, the doctor inputs the desired second set period value to the box 68B using the operation section 46.

The doctor then uses the operation section 46 to press (click on) a button 70 displayed on the advice screen 60 to instruct recalculation.

When the doctor presses the button 70, affirmative determination is made in step S124, and processing proceeds to step S126. In step S126, the controller 40 acquires the setting values input to the box 66A, the box 66B, the box 68A, and the box 68B, and then processing returns to step S100 and the processing of each of the above steps is repeated.

When the doctor has not pressed the button 70, negative determination is made in step S124, and processing proceeds to step S128. In step S128, the controller 40 determines whether or not to end the presentation processing. The criteria used to determine whether or not to end the presentation processing are not particularly limited. For example, the doctor using the operation section 46 to press a non-illustrated button displayed on the advice screen 60 to instruct display or instruct closing of the daily fluctuation graph display screen 50 may be set as a criterion, and the presentation processing may be ended when this criterion has been met. In cases in which this criterion is not met, negative determination is made in step S128, and processing returns to step S120. In cases in which this criterion has been met, affirmative determination is made in step S128, and the presentation processing is ended.

In this manner, in the present exemplary embodiment, the display device 16 determines time bands in which the user U is in a low blood glucose state and time bands in which the user U is in a high blood glucose state based on the continuous blood glucose measurement data 31A for the user U measured by the continuous blood glucose measurement device 14, and presents the determined time periods as measurement time periods for the user to measure their blood glucose level using the blood glucose self-measurement device 12. Accordingly, the display device 16 of the present exemplary embodiment may present appropriate measurement time periods at which to take measurements using the blood glucose self-measurement device 12.

Second Exemplary Embodiment

As described above, fewer blood glucose level measurements are taken by the blood glucose self-measurement device 12 than by the continuous blood glucose measurement device 14. As a result, differences arise between the blood glucose levels (blood glucose level fluctuations) of the user U in the blood glucose self-measurement data 21A from the blood glucose self-measurement device 12 and the glucose levels (blood glucose level fluctuations) of the user U in the continuous blood glucose measurement data 31A from the continuous blood glucose measurement device 14.

The present exemplary embodiment describes a configuration in which a time band for which there is a small number of measurements taken by the blood glucose self-measurement device 12 (referred to hereafter as "number of self-measurements") is presented as an appropriate measurement time period for measuring blood glucose level using the blood glucose self-measurement device 12, regardless of whether or not this time band is a time band in which there is a strong tendency for the user U to be in a high blood glucose state or conversely, a time band in which there is a strong tendency for the user U to be in a low blood glucose state.

A blood glucose measurement system 10, blood glucose self-measurement device 12, continuous blood glucose measurement device 14, and display device 16 of the present exemplary embodiment are similar in configuration to those of the first exemplary embodiment, and so explanation thereof is omitted.

Moreover, display of a daily fluctuation graph display screen 50 on the display device 16 is also similar to in the first exemplary embodiment, and so explanation thereof is omitted. The daily fluctuation graph display screen 50 includes a self-measurement daily fluctuation graph 52 based on blood glucose self-measurement data 21A (second information) from the blood glucose self-measurement device 12, and a continuous measurement daily fluctuation graph 54 based on continuous blood glucose measurement data 31A (first information) from the continuous blood glucose measurement device 14.

In the present exemplary embodiment, presentation processing executed by the controller 40 of the display device 16 differs in part from the presentation processing executed by the controller 40 of the display device 16 of the first exemplary embodiment (see FIG. 8). Explanation follows regarding the processing that is different.

Figure 11:
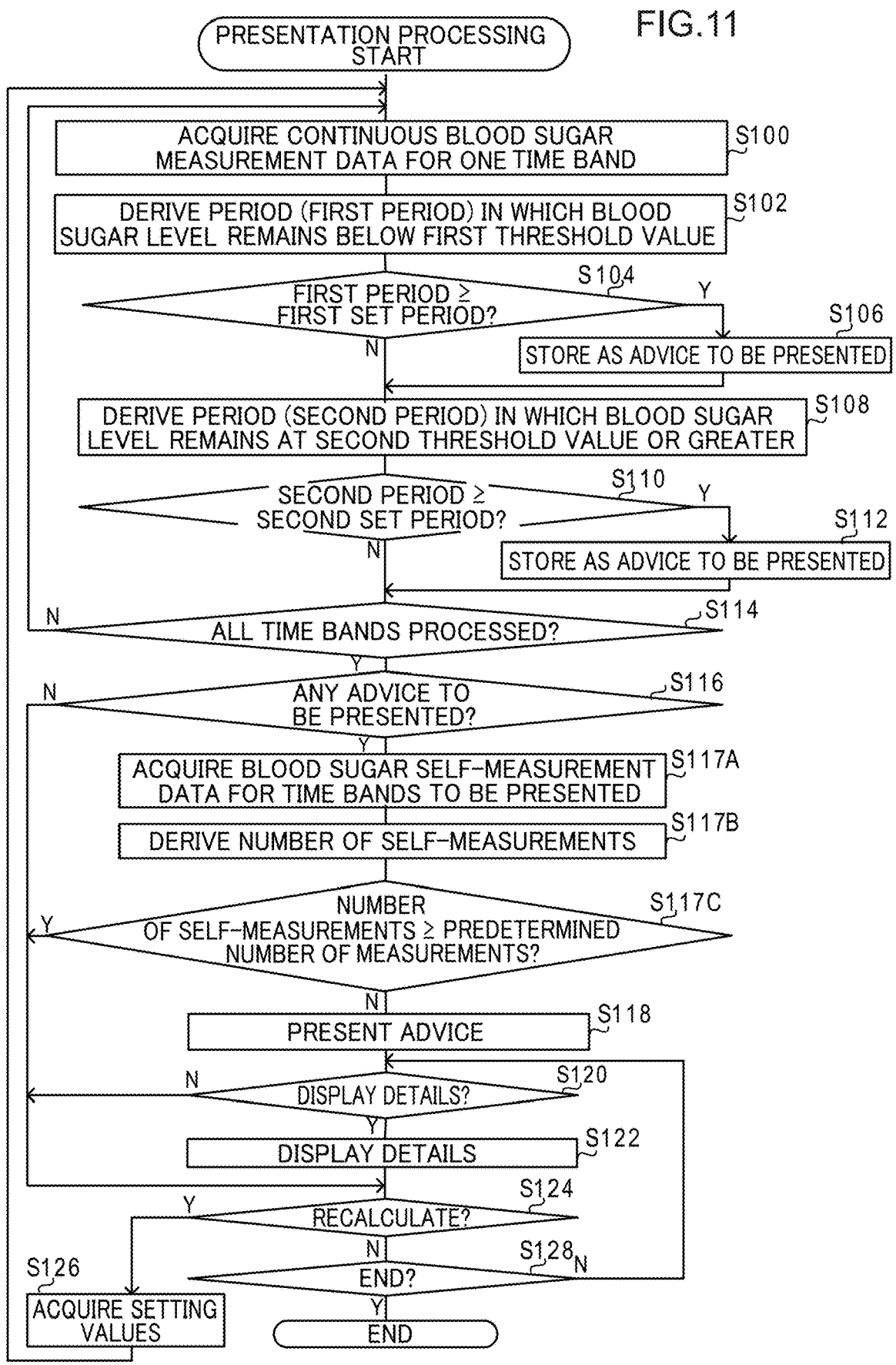
FIG. 11 is a flowchart illustrating a presentation processing executed by a display device of a second exemplary embodiment.

FIG. 11 is a flowchart illustrating a flow of presentation processing executed by the controller 40 of the display device 16 of the present exemplary embodiment. As illustrated in FIG. 11, the presentation processing of the present exemplary embodiment differs from the presentation processing of the first exemplary embodiment (see FIG. 8) in the point that the processing of steps S117A to S117C is executed between step S116 and step S118.

In the presentation processing of the present exemplary embodiment, when information representing advice to be presented has been saved in the RAM 40C, affirmative determination is made in step S116, and processing proceeds to step S117A.

In step S117A, from the storage section 41, the controller 40 acquires blood glucose self-measurement data 21A for the time band corresponding to the advice to be presented. At the next step S117B, the controller 40 determines the number of self-measurements in the blood glucose self-measurement data 21A. Note that, in cases in which the user U has not taken any blood glucose level measurements using the blood glucose self-measurement device 12 in the time band corresponding to the advice to be presented, the blood glucose self-measurement data 21A does not include any data corresponding to that time band. In such cases, in step S117A, the controller 40 of the present exemplary embodiment does not acquire the blood glucose self-measurement data 21A, and in step S117B, the controller 40 determines the number of self-measurements to be 0.

At the next step S117C, the controller 40 determines whether or not the number of self-measurements determined in step S117B is a predetermined number of self-measurements or greater. The predetermined number of self-measurements is a threshold value used to determine whether or not there are a sufficient number of self-measurements for the user U to recognize that they are in a low blood glucose state, a high blood glucose state, or a state that is neither a low blood glucose state nor a high blood glucose state. Namely, in the present exemplary embodiment, in cases in which the number of self-measurements is fewer than the predetermined number of self-measurements for each time band, there is considered to be a possibility that the user U could be in a low blood glucose state or a high blood glucose state, but unable to adequately recognize that they were in such a state.

In the present exemplary embodiment, in cases in which the number of self-measurements is the predetermined number of self-measurements or greater for all time bands, it is considered that the user U would be able to recognize that they are in a low blood glucose state or a high blood glucose state, based on the blood glucose level measurement results of the blood glucose self-measurement device 12, and so measurement points are not presented. Accordingly, affirmative determination is made in step S117C, and processing proceeds to step S120.

However, in cases in which the number of self-measurements is fewer than the predetermined number of self-measurements in even one time band, negative determination is made in step S117C, and processing proceeds to step S118. In step S118, an advice screen 60 is generated and displayed on the display 44.

Note that in the processing of step S118, the advice screen 60 generated by the controller 40 and displayed on the display 44 differs in part from the advice screen 60 of the first exemplary embodiment (see FIG. 9 and FIG. 10). FIG. 12 illustrates an example of the advice screen 60 of the present exemplary embodiment.

As illustrated in FIG. 12, the advice 63 displayed on the advice screen 60 of the present exemplary embodiment displays the number of self-measurements (see "Number of SMBG measurements") for each time band.

As illustrated in FIG. 12, the advice screen 60 displays update information 72 for updating the predetermined number of self-measurements, update information 66 for updating the first threshold value and the first set period used to determine a low blood glucose state, and update information 68 for updating the second threshold value and the second set period used to determine a high blood glucose state. The update information 72 includes a box 72A for setting the predetermined number of measurements. Note that the box 72A displays the value that is currently set.

To update the predetermined number of self-measurements, the doctor inputs the desired predetermined number of self-measurements to the box 72A using the operation section 46. The doctor then uses the operation section 46 to press (click on) the button 70 displayed on the advice screen 60 to instruct recalculation.

Accordingly, in step S126 of the present exemplary embodiment, the controller 40 acquires the setting values input to the box 66A, the box 66B, the box 68A, the box 68B, and the box 72A, and then processing returns to step S100 and the processing of each of the above steps is repeated.

In this manner, in the present exemplary embodiment, regardless of whether the user U is in a low blood glucose state or a high blood glucose state, the display device 16 presents time bands in which there are too few blood glucose level measurements by the blood glucose self-measurement device 12 as appropriate measurement time periods at which to take measurements using the blood glucose self-measurement device 12. Accordingly, the display device 16 of the present exemplary embodiment may present appropriate measurement time periods at which to take measurements using the blood glucose self-measurement device 12.

Third Exemplary Embodiment

In the exemplary embodiments described above, explanation has been given regarding configurations in which measurement time periods are determined and presented according to time bands. However, in the present exemplary embodiment, explanation is given regarding a configuration in which measurement time periods are determined and presented without using time bands.

A blood glucose measurement system 10, blood glucose self-measurement device 12, continuous blood glucose measurement device 14, and display device 16 of the present exemplary embodiment are similar in configuration to those of the first exemplary embodiment, and so explanation thereof is omitted.

Moreover, display of a daily fluctuation graph display screen 50 on the display device 16 is also similar to in the first exemplary embodiment, and so explanation thereof is omitted. The daily fluctuation graph display screen 50 includes a self-measurement daily fluctuation graph 52 based on blood glucose self-measurement data 21A (second information) from the blood glucose self-measurement device 12, and a continuous measurement daily fluctuation graph 54 based on continuous blood glucose measurement data 31A (first information) from the continuous blood glucose measurement device 14.

In the present exemplary embodiment, presentation processing executed by the controller 40 of the display device 16 differs in part from the presentation processing (see FIG. 8) executed by the controller 40 of the display device 16 of the first exemplary embodiment. Explanation follows regarding the processing that is different.

Figure 13:
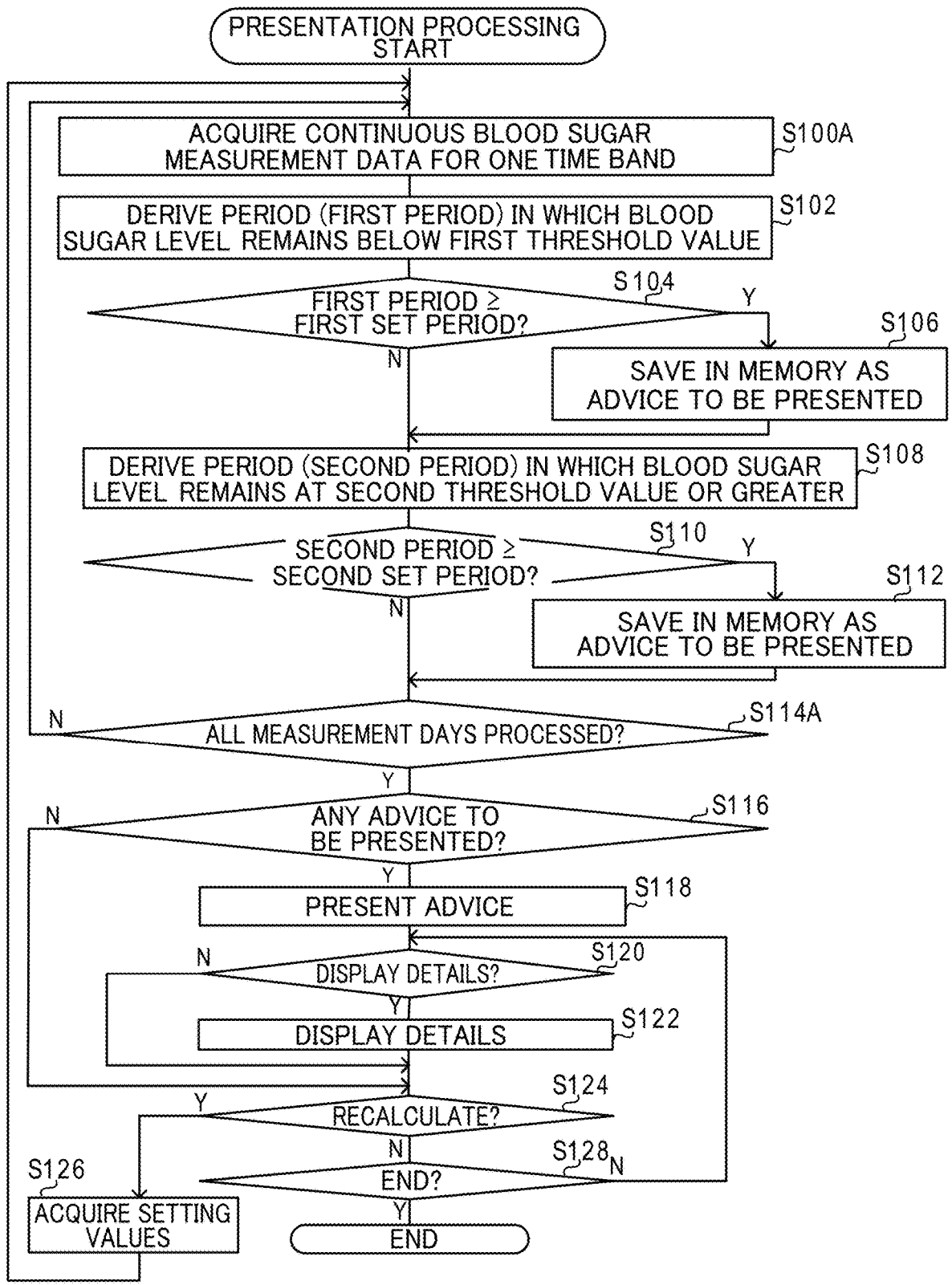
FIG. 13 is a flowchart illustrating a presentation processing executed by a display device of a third exemplary embodiment.

FIG. 13 is a flowchart illustrating a flow of presentation processing executed by the controller 40 of the display device 16 of the present exemplary embodiment. As illustrated in FIG. 13, the presentation processing of the present exemplary embodiment differs from the presentation processing of the first exemplary embodiment (see FIG. 8) in that that the processing of step S100A is executed instead of step S100, and the processing of step S114A is executed instead of step S114.

As illustrated in FIG. 13, in the presentation processing of the present exemplary embodiment, in step S100A, the controller 40 acquires continuous blood glucose measurement data 31A for one measurement day from the storage section 41. Namely, the controller 40 acquires one day's worth (24 hours' worth) of continuous blood glucose measurement data 31A. In this manner, in the present exemplary embodiment, instead of using the time bands of the exemplary embodiments described above, the advice to be presented is determined for each measurement day.

Accordingly, in the present exemplary embodiment, in step S106, all first periods of the first set period or longer in the 24 hours' worth of continuous blood glucose measurement data 31A are stored in the RAM 40C as advice to be presented. Moreover, in step S112, all second periods of the second set period or longer in the 24 hours' worth of continuous blood glucose measurement data 31A are saved in the RAM 40C as advice to be presented.

Then, in step S114A, the controller 40 determines whether or not the processing of step S100A to step S112 has been performed for all measurement days. In cases in which the processing of step S100A to step S112 has not yet been performed for all measurement days, negative determination is made in step S114A, and the processing returns to step S100A. The controller 40 then acquires the continuous blood glucose measurement data 31A and executes the processing of S100A to step S112 for a measurement day for which the processing of step S100A to step S112 has not yet been performed.

Accordingly, in the present exemplary embodiment, the first period and the second period for which advice is to be presented are presented as measurement points.

In this manner, in the display device 16 of the present exemplary embodiment, first periods in which the user U is in a low blood glucose state and second periods in which the user U is in a high blood glucose state are determined based on the continuous blood glucose measurement data 31A for the user U measured by the continuous blood glucose measurement device 14. The determined first periods and second periods are presented as measurement time periods for the user U to measure their blood glucose level using the blood glucose self-measurement device 12. Accordingly, the display device 16 of the present exemplary embodiment may present appropriate measurement time periods at which to take measurements using the blood glucose self-measurement device 12.

As described above, the display device 16 of the present exemplary embodiment acquires the continuous blood glucose measurement data 31A, in which measurement results of the glucose level of the user U measured at predetermined time intervals by the continuous blood glucose measurement device 14 are associated with measurement times at which the measurements were taken. Based on the acquired continuous blood glucose measurement data 31A, the display device 16 determines and presents time periods for the user U to take self-monitoring blood glucose level measurements using the blood glucose self-measurement device 12.

Accordingly, the display device 16 of the exemplary embodiments described above may present appropriate measurement time periods for the user U to measure their blood glucose level using the blood glucose self-measurement device 12.

Moreover, the display device 16 of the exemplary embodiments described above determines measurement time periods using the continuous blood glucose measurement data 31A for individual users U. This thereby enables appropriate measurement time periods to be presented for individual users U.

Even without using the display device 16 to present measurement time periods with the display device 16 of the exemplary embodiments described above, the user U as able to appropriately recognize their own blood glucose level state by self-measurement using the blood glucose self-measurement device 12. This thereby enables the user U to avoid the annoyance of having the sensor 38A of the continuous blood glucose measurement device 14 constantly attached to their skin.

Note that the present disclosure is not limited to the exemplary embodiments described above, and obviously various modifications and combinations of the exemplary embodiments are possible.

For example, the exemplary embodiments described above are limited to configurations in which the display device 16 performs determinations to determine and present measurement points for both low blood glucose states and high blood glucose states. However, there is no limitation to such a configuration. The display device 16 may perform determinations to present measurement points for either one of these states.

In the exemplary embodiments described above, detailed description has been given regarding configurations in which the continuous blood glucose measurement device 14 is a measurement device used for CGM. However, the measurement device is not limited thereto. Any measurement device would suffice therefor so long as it measures the glucose level of the user U continuously at predetermined time intervals, and generally at least takes a greater number of measurements than the blood glucose self-measurement device 12 in each time band. For example, the continuous blood glucose measurement device 14 may be a measurement device used for FGM. Moreover, detailed description has been given regarding configurations in which the blood glucose self-measurement device 12 is a measurement device used for SMBG However, the measurement device is not limited thereto. Any measurement device would suffice therefor so long as the user uses it to measure their own blood glucose levels at given time periods.

In the exemplary embodiments described above, explanation has been given regarding configurations in which the first threshold value, the first set period, the second threshold value, the second set period, and the predetermined number of measurements all have predetermined initial values, with these initial value being used when presentation processing is started. However, there is no limitation to such a configuration. For example, configuration may be made in which the controller 40 of the display device 16 stores values that were used when performing presentation processing, and the next time presentation processing is executed for the same user U, the previously stored values are employed.

It goes without saying that the daily fluctuation graph display screen 50 and the advice screen 60 are merely examples. For example, although the advice screen 60 is configured so as to display only the start time of each time band in the advice 63, configuration may be made such that the end time of each time band is also displayed.

Moreover, the mode used to present the measurement points is not limited to display on the display 44 of the display device 16. For example, the measurement points may be displayed on another device, such as a portable device in the possession of the user U. Additionally, there is no limitation to a visual display as described above, and, for example, the measurement points may be presented using an audible display presented by audio.

Moreover, in the exemplary embodiments described above, an example has been given in which the presentation program is read from the ROM 40B. However, there is no requirement for the presentation program to be stored on the ROM 40B initially. For example, the presentation program may initially be stored on any portable storage medium, such as a Solid State Drive (SSD), Universal Serial Bus (USB) memory, or Compact Disc Read Only Memory (CD-ROM). In such cases, the presentation program on the storage medium is installed in the display device 16 and stored in the ROM 40B, and the presentation program stored in the ROM 40B is then executed by the CPU 40A.

All cited documents, patent applications, and technical standards mentioned in the present specification are incorporated by reference in the present specification to the same extent as if each individual cited document, patent application, or technical standard was specifically and individually indicated to be incorporated by reference.

What is claimed is:

1. A presentation method for presenting a time period for each of a plurality of time bands obtained by dividing one day into the plurality of time bands to measure a blood glucose level, the presentation method comprising:
    acquiring first information, the first information including a measurement result in which a glucose level of a user is measured with a time interval using a first measurement device and a measurement time at which the measurement result was acquired;
    determining, based on a comparison result obtained by comparing the first information with a predetermined threshold of the glucose level and a preset period, the time period for each of the plurality of time bands for the user to measure the blood glucose level by using a second measurement device;
    acquiring second information, the second information including a measurement result for a blood glucose level of the user by the second measurement device and a measurement time at which the measurement result was acquired;

determining, based on the second information, a number of measurements measured by the second measurement device for each of the plurality of time bands; and in a case in which there is a time band that has a number of measurements that is equal to or fewer than a predetermined number of measurements, determining the time period for each time band that has a number of measurements that is equal to or fewer than the predetermined number of measurements, and presenting the time period for each of a plurality of time bands at a display.

2. The presentation method of claim 1, wherein determining the time period includes:

comparing the first information with a first threshold value which is the predetermined threshold of the glucose level and a first set period which is the preset period; and determining a first period as the time period in a case in which the first period is equal to or longer than the first set period, the first period being a period in which the glucose level included in the first information is continuously equal to or lower than the first threshold value.

3. The presentation method of claim 1, wherein determining the time period includes:

comparing the first information with a second threshold value which is the predetermined threshold of the glucose level and a second set period which is the preset period; and determining a second period as the time period in a case in which the second period is equal to or longer than the second set period, the second period being a period in which the glucose level included in the first information is continuously equal to or greater than the second threshold value.

4. The presentation method of claim 1, wherein the first measurement device is a device that employs a sensor attached to skin of the user to measure glucose levels.

5. The presentation method of claim 1, wherein the first measurement device is a device that employs a sensor to measure glucose levels in an interstitial fluid of the user, and that is used for Continuous Glucose Monitoring (CGM) or Flash Glucose Monitoring (FGM).

6. The presentation method of claim 1, wherein the second measurement device is a device used for Self Monitoring of Blood Glucose (SMBG) used by the user.

7. A presentation device comprising:

an acquisition section acquiring first information, the first information including a measurement result in which a glucose level of a user is measured with a time interval using a first measurement device and a measurement time at which the measurement result was acquired;

a determination section determining, based on a comparison result obtained by comparing the first information with a predetermined threshold of the glucose level and a preset period, a time period for each of a plurality of time bands obtained by dividing one day into the plurality of time bands for the user to measure a blood glucose level by using a second measurement device; wherein:

the acquisition section acquires second information, the second information including a measurement result for a blood glucose level of the user by the second measurement device and a measurement time at which the measurement result was acquired, the determination section determines, based on the second information, a number of measurements measured by the second measurement device for each of the plurality of time bands, in a case in which there is a time band that has a number of measurements that is equal to or fewer than a predetermined number of measurements, the determination section determines the time period for each time band that has a number of measurements that is equal to or fewer than the predetermined number of measurements, and a presentation section presenting the time period for each of a plurality of time bands at a display.

8. A non-transitory computer readable medium storing a program that is executable by a computer to perform a process for presenting a time period for each of a plurality of time bands obtained by dividing one day into the plurality of time bands to measure a blood glucose level, the process comprising:

acquiring first information, the first information including a measurement result in which a glucose level of a user is measured with a time interval using a first measurement device and a measurement time at which the measurement result was acquired;

determining, based on a comparison result obtained by comparing the first information with a predetermined threshold of the glucose level and a preset period, the time period for each of the plurality of time bands for the user to measure the blood glucose level by using a second measurement device;

acquiring second information for each of the plurality of time bands, the second information including a measurement result for a blood glucose level of the user by the second measurement device and a measurement time at which the measurement result was acquired;

determining, based on the second information, a number of measurements measured by the second measurement device for each of the plurality of time bands;

in a case in which there is a time band that has a number of measurements that is equal to or fewer than a predetermined number of measurements, determining the time period for each of the time bands that has a number of measurements that is equal to or fewer than the predetermined number of measurements; and presenting the time period for each of a plurality of time bands at a display.

* * * * *